US008657803B2

(12) United States Patent
Helmerson et al.

(10) Patent No.: US 8,657,803 B2
(45) Date of Patent: Feb. 25, 2014

(54) DEVICE FOR PROVIDING FLUID TO A RECEPTACLE

(75) Inventors: Elisabet Helmerson, Billdal (SE); Fredrik Backstrom, Vastra Frolunda (SE); Anna Ellstrom, Molndal (SE)

(73) Assignee: Carmel Pharma AB, Goteborg (SE)

( * ) Notice: Subject to any disclaimer, the term of this patent is extended or adjusted under 35 U.S.C. 154(b) by 231 days.

(21) Appl. No.: 11/762,543

(22) Filed: Jun. 13, 2007

(65) Prior Publication Data

US 2008/0312634 A1 Dec. 18, 2008

(51) Int. Cl.

| | |
|---|---|
| ***A61M 5/32*** | (2006.01) |
| ***A61J 1/00*** | (2006.01) |
| ***A61J 1/05*** | (2006.01) |
| ***A61J 1/06*** | (2006.01) |

(52) U.S. Cl.
USPC ........... 604/414; 604/403; 604/404; 604/405; 604/411; 604/415; 604/416

(58) Field of Classification Search
USPC ................. 604/403, 404, 405, 411, 415, 416; 141/929; 137/625
See application file for complete search history.

(56) References Cited

U.S. PATENT DOCUMENTS

| | | | |
|---|---|---|---|
| 1,844,342 | A | 2/1932 | Berman |
| 2,010,417 | A | 8/1935 | Schwab |
| 2,697,438 | A | 12/1954 | Hickey |
| 2,717,599 | A | 9/1955 | Huber |
| 3,064,651 | A | 11/1962 | Henderson |
| 3,071,135 | A | 1/1963 | Baldwin et al. |
| 3,308,822 | A | 3/1967 | DeLuca |
| 3,316,908 | A | 5/1967 | Burke |
| 3,340,671 | A | 9/1967 | Loo |
| 3,390,677 | A | 7/1968 | Razimbaud |
| 3,448,740 | A | 6/1969 | Figge |
| 3,542,240 | A | 11/1970 | Solowey |
| 3,783,895 | A | 1/1974 | Weichselbaum |
| 3,788,320 | A | 1/1974 | Dye |
| 3,822,700 | A | 7/1974 | Pennington |
| 3,938,520 | A | 2/1976 | Scislowicz et al. |
| 3,976,073 | A | 8/1976 | Quick et al. |
| 4,096,860 | A | 6/1978 | McLaughlin |
| 4,296,786 | A | 10/1981 | Brignola |
| D270,568 | S | 9/1983 | Armstrong |

(Continued)

FOREIGN PATENT DOCUMENTS

| | | |
|---|---|---|
| AU | 200112863 | 5/2003 |
| DE | 2005519 | 10/1979 |

(Continued)

OTHER PUBLICATIONS

Infoplease dictionary entry for "integrated." http://dictionary.infoplease.com/integrated. Accessed Apr. 24, 2013.*

(Continued)

*Primary Examiner* — Adam Marcetich
(74) *Attorney, Agent, or Firm* — Servilla Whitney LLC

(57) ABSTRACT

A device for providing sterilized or cleaned fluid to a receptacle and thereby facilitate conveyance of a substance out of the receptacle, comprising a connector and a container which form an integrated unit. The connector is provided with a first means for connection to a receptacle. Sterilized or cleaned fluid is transferred from the container to the receptacle.

14 Claims, 9 Drawing Sheets

(56) References Cited

U.S. PATENT DOCUMENTS

| | | | | | |
|---|---|---|---|---|---|
| 4,490,139 | A | | 12/1984 | Huizenga et al. | |
| 4,516,967 | A | | 5/1985 | Kopfer | |
| 4,564,054 | A | * | 1/1986 | Gustavsson | 141/329 |
| 4,573,967 | A | | 3/1986 | Hargrove et al. | |
| 4,576,211 | A | | 3/1986 | Valentini et al. | |
| 4,581,016 | A | | 4/1986 | Gettig | |
| 4,582,223 | A | | 4/1986 | Kobe | |
| 4,588,403 | A | | 5/1986 | Weiss et al. | |
| 4,600,040 | A | * | 7/1986 | Naslund | 141/18 |
| 4,623,343 | A | | 11/1986 | Thompson | |
| 4,629,455 | A | | 12/1986 | Kanno | |
| 4,632,673 | A | | 12/1986 | Tiitola et al. | |
| 4,636,204 | A | | 1/1987 | Christopherson et al. | |
| 4,673,400 | A | | 6/1987 | Martin | |
| 4,673,404 | A | * | 6/1987 | Gustavsson | 604/411 |
| 4,737,150 | A | | 4/1988 | Baeumle et al. | |
| 4,752,287 | A | | 6/1988 | Kurtz et al. | |
| 4,759,756 | A | | 7/1988 | Forman et al. | |
| 4,768,568 | A | | 9/1988 | Fournier et al. | |
| 4,792,329 | A | | 12/1988 | Schreuder | |
| 4,804,015 | A | | 2/1989 | Albinsson | |
| 4,822,340 | A | | 4/1989 | Kamstra | |
| 4,826,492 | A | | 5/1989 | Magasi | |
| 4,834,717 | A | | 5/1989 | Haber et al. | |
| 4,842,585 | A | | 6/1989 | Witt | |
| 4,850,978 | A | | 7/1989 | Dudar et al. | |
| 4,864,717 | A | | 9/1989 | Baus, Jr. | |
| 4,872,494 | A | | 10/1989 | Coccia | |
| 4,878,897 | A | | 11/1989 | Katzin | |
| 4,889,529 | A | | 12/1989 | Haindl | |
| 4,898,209 | A | | 2/1990 | Zbed | |
| 4,909,290 | A | | 3/1990 | Coccia | |
| 4,932,937 | A | | 6/1990 | Gustavsson et al. | |
| 4,944,736 | A | | 7/1990 | Holtz | |
| 4,964,855 | A | | 10/1990 | Todd et al. | |
| 4,982,769 | A | | 1/1991 | Fournier et al. | |
| 4,994,048 | A | | 2/1991 | Metzger | |
| 4,997,083 | A | | 3/1991 | Loretti et al. | |
| 5,017,186 | A | * | 5/1991 | Arnold | 604/48 |
| 5,041,105 | A | | 8/1991 | D'Alo et al. | |
| 5,061,264 | A | | 10/1991 | Scarrow | |
| 5,071,413 | A | | 12/1991 | Utterberg | |
| 5,122,116 | A | | 6/1992 | Kriesel et al. | |
| 5,122,123 | A | | 6/1992 | Vaillancourt | |
| 5,137,524 | A | | 8/1992 | Lynn et al. | |
| 5,158,554 | A | | 10/1992 | Jepson et al. | |
| 5,199,947 | A | | 4/1993 | Lopez et al. | |
| 5,201,725 | A | | 4/1993 | Kling | |
| 5,207,658 | A | | 5/1993 | Rosen et al. | |
| 5,232,109 | A | | 8/1993 | Tirrell et al. | |
| 5,254,097 | A | | 10/1993 | Schock et al. | |
| 5,279,583 | A | | 1/1994 | Shober, Jr. et al. | |
| 5,279,605 | A | | 1/1994 | Karrasch et al. | |
| 5,308,347 | A | | 5/1994 | Sunago et al. | |
| 5,328,480 | A | | 7/1994 | Melker et al. | |
| 5,334,163 | A | * | 8/1994 | Sinnett | 604/236 |
| 5,356,406 | A | | 10/1994 | Schraga | |
| 5,385,545 | A | | 1/1995 | Kriesel et al. | |
| 5,385,547 | A | | 1/1995 | Wong et al. | |
| 5,389,085 | A | | 2/1995 | D'Alessio et al. | |
| 5,405,326 | A | | 4/1995 | Haber et al. | |
| 5,445,630 | A | | 8/1995 | Richmond | |
| 5,447,501 | A | | 9/1995 | Karlsson et al. | |
| 5,456,675 | A | | 10/1995 | Wolbring et al. | |
| 5,470,522 | A | | 11/1995 | Thome et al. | |
| 5,478,328 | A | | 12/1995 | Silverman et al. | |
| 5,478,337 | A | | 12/1995 | Okamoto et al. | |
| 5,492,531 | A | | 2/1996 | Post et al. | |
| 5,514,117 | A | | 5/1996 | Lynn | |
| 5,515,871 | A | | 5/1996 | Bittner et al. | |
| 5,536,259 | A | | 7/1996 | Utterberg | |
| 5,575,780 | A | | 11/1996 | Saito | |
| 5,593,028 | A | | 1/1997 | Haber et al. | |
| 5,613,954 | A | | 3/1997 | Nelson et al. | |
| 5,632,735 | A | | 5/1997 | Wyatt et al. | |
| 5,647,845 | A | | 7/1997 | Haber et al. | |
| 5,685,866 | A | | 11/1997 | Lopez | |
| 5,752,942 | A | | 5/1998 | Doyle et al. | |
| 5,766,147 | A | | 6/1998 | Sancoff et al. | |
| 5,766,211 | A | | 6/1998 | Wood et al. | |
| 5,782,872 | A | | 7/1998 | Muller | |
| 5,795,336 | A | | 8/1998 | Romano et al. | |
| 5,817,083 | A | | 10/1998 | Shemesh et al. | |
| 5,820,609 | A | | 10/1998 | Saito | |
| 5,827,262 | A | | 10/1998 | Neftel et al. | |
| 5,837,262 | A | | 11/1998 | Golubev et al. | |
| 5,875,931 | A | | 3/1999 | Py | |
| 5,879,345 | A | | 3/1999 | Aneas | |
| 5,897,526 | A | | 4/1999 | Vaillancourt | |
| 5,934,510 | A | | 8/1999 | Anderson | |
| 5,984,899 | A | | 11/1999 | D'Alessio et al. | |
| 6,063,068 | A | | 5/2000 | Fowles et al. | |
| D427,308 | S | | 6/2000 | Zinger | |
| 6,070,623 | A | | 6/2000 | Aneas | |
| 6,071,270 | A | | 6/2000 | Fowles et al. | |
| 6,090,091 | A | | 7/2000 | Fowles et al. | |
| 6,113,068 | A | | 9/2000 | Ryan | |
| 6,113,583 | A | | 9/2000 | Fowles et al. | |
| 6,142,446 | A | | 11/2000 | Leinsing | |
| 6,146,362 | A | | 11/2000 | Turnbull et al. | |
| 6,209,738 | B1 | | 4/2001 | Jansen et al. | |
| 6,221,065 | B1 | | 4/2001 | Davis | |
| 6,245,056 | B1 | | 6/2001 | Walker et al. | |
| D445,501 | S | | 7/2001 | Niedospial, Jr. | |
| 6,253,804 | B1 | | 7/2001 | Safabash | |
| 6,258,078 | B1 | | 7/2001 | Thilly | |
| 6,343,629 | B1 | * | 2/2002 | Wessman et al. | 141/383 |
| 6,364,865 | B1 | * | 4/2002 | Lavi et al. | 604/411 |
| 6,387,074 | B1 | | 5/2002 | Horppu et al. | |
| 6,453,956 | B2 | | 9/2002 | Safabash | |
| 6,471,674 | B1 | | 10/2002 | Emig et al. | |
| 6,517,523 | B1 | | 2/2003 | Kaneko et al. | |
| 6,537,263 | B1 | | 3/2003 | Aneas | |
| 6,551,299 | B2 | * | 4/2003 | Miyoshi et al. | 604/403 |
| 6,571,837 | B2 | | 6/2003 | Jansen et al. | |
| 6,591,876 | B2 | | 7/2003 | Safabash | |
| 6,644,367 | B1 | | 11/2003 | Savage et al. | |
| 6,685,692 | B2 | | 2/2004 | Fathallah | |
| 6,715,520 | B2 | | 4/2004 | Andreasson et al. | |
| 6,761,286 | B2 | | 7/2004 | Py et al. | |
| D495,416 | S | | 8/2004 | Dimeo et al. | |
| 6,786,244 | B1 | | 9/2004 | Jones | |
| D506,256 | S | | 6/2005 | Miyoshi et al. | |
| 6,960,194 | B2 | | 11/2005 | Hommann et al. | |
| 7,000,806 | B2 | | 2/2006 | Py et al. | |
| 7,080,672 | B2 | | 7/2006 | Fournie et al. | |
| 7,297,140 | B2 | | 11/2007 | Orlu et al. | |
| D570,477 | S | | 6/2008 | Gallogly et al. | |
| D572,820 | S | | 7/2008 | Gallogly et al. | |
| D577,438 | S | | 9/2008 | Gallogly et al. | |
| D577,822 | S | | 9/2008 | Gallogly et al. | |
| D582,033 | S | | 12/2008 | Baxter et al. | |
| D605,755 | S | | 12/2009 | Baxter et al. | |
| 7,703,486 | B2 | | 4/2010 | Costanzo | |
| D616,984 | S | | 6/2010 | Gilboa | |
| 7,744,581 | B2 | | 6/2010 | Wallen et al. | |
| 8,167,863 | B2 | * | 5/2012 | Yow | 604/406 |
| 8,323,237 | B2 | * | 12/2012 | Radmer et al. | 604/89 |
| 2001/0021825 | A1 | | 9/2001 | Becker et al. | |
| 2001/0025671 | A1 | | 10/2001 | Safabash | |
| 2002/0002352 | A1 | | 1/2002 | Becker et al. | |
| 2002/0004643 | A1 | * | 1/2002 | Carmel et al. | 604/86 |
| 2002/0069616 | A1 | * | 6/2002 | Odell et al. | 53/425 |
| 2002/0082586 | A1 | | 6/2002 | Finley et al. | |
| 2002/0127150 | A1 | | 9/2002 | Sasso | |
| 2002/0177819 | A1 | | 11/2002 | Barker et al. | |
| 2003/0010717 | A1 | | 1/2003 | Brugger et al. | |
| 2003/0070726 | A1 | * | 4/2003 | Andreasson et al. | 141/329 |
| 2003/0106610 | A1 | | 6/2003 | Roos et al. | |
| 2003/0107628 | A1 | | 6/2003 | Fowles et al. | |
| 2003/0233083 | A1 | | 12/2003 | Houwaert et al. | |
| 2004/0039346 | A1 | * | 2/2004 | Baldwin et al. | 604/236 |
| 2004/0116858 | A1 | | 6/2004 | Heinz et al. | |
| 2004/0199139 | A1 | | 10/2004 | Fowles et al. | |

(56) References Cited

U.S. PATENT DOCUMENTS

| | | | | |
|---|---|---|---|---|
| 2004/0215147 | A1* | 10/2004 | Wessman et al. | 604/187 |
| 2004/0249341 | A1* | 12/2004 | Newbrough et al. | 604/87 |
| 2005/0215977 | A1 | 9/2005 | Uschold | |
| 2006/0025747 | A1 | 2/2006 | Sullivan et al. | |
| 2006/0064070 | A1* | 3/2006 | Martin | 604/403 |
| 2006/0106360 | A1 | 5/2006 | Wong | |
| 2006/0111667 | A1 | 5/2006 | Matsuura et al. | |
| 2006/0157984 | A1 | 7/2006 | Rome et al. | |
| 2006/0186045 | A1 | 8/2006 | Jensen et al. | |
| 2007/0021725 | A1 | 1/2007 | Villette | |
| 2007/0060841 | A1 | 3/2007 | Henshaw | |
| 2007/0088313 | A1 | 4/2007 | Zinger et al. | |
| 2007/0106244 | A1* | 5/2007 | Mosler et al. | 604/411 |
| 2007/0179441 | A1 | 8/2007 | Chevallier | |
| 2007/0270759 | A1 | 11/2007 | Pessin | |
| 2007/0270778 | A9 | 11/2007 | Zinger et al. | |
| 2008/0045919 | A1* | 2/2008 | Jakob et al. | 604/406 |
| 2008/0103453 | A1 | 5/2008 | Liversidge | |
| 2008/0103485 | A1 | 5/2008 | Kruger | |
| 2008/0142388 | A1* | 6/2008 | Whitley et al. | 206/438 |
| 2008/0172039 | A1 | 7/2008 | Raines | |
| 2008/0223484 | A1 | 9/2008 | Horppu | |
| 2008/0287920 | A1 | 11/2008 | Fangrow et al. | |
| 2008/0312634 | A1 | 12/2008 | Helmerson et al. | |
| 2009/0254042 | A1 | 10/2009 | Gratwohl et al. | |
| 2010/0137827 | A1 | 6/2010 | Warren et al. | |
| 2010/0204671 | A1 | 8/2010 | Kraushaar et al. | |
| 2010/0243099 | A1 | 9/2010 | Yodfat | |

FOREIGN PATENT DOCUMENTS

| | | |
|---|---|---|
| EP | 0255025 | 2/1988 |
| EP | 0259582 | 3/1988 |
| EP | 0285424 | 10/1988 |
| EP | 0311787 | 4/1989 |
| EP | 0376629 | 7/1990 |
| EP | 0803267 | 10/1997 |
| EP | 0819442 | 1/1998 |
| EP | 0995453 | 4/2000 |
| EP | 1060730 | 12/2000 |
| EP | 1731128 | 12/2006 |
| FR | 2757405 | 6/1998 |
| FR | 2780878 | 1/2000 |
| GB | 1579065 | 11/1980 |
| JP | 49-12690 | 5/1972 |
| JP | 55-156748 | 11/1980 |
| JP | 01-123653 | 5/1989 |
| JP | 288664 | 7/1990 |
| JP | 3030963 | 8/1996 |
| JP | 2000167022 | 6/2000 |
| JP | 2001505092 | 4/2001 |
| JP | 2001293085 | 10/2001 |
| TW | 482670 | 4/2002 |
| WO | WO 84/04672 | 12/1984 |
| WO | WO 84/04673 | 12/1984 |
| WO | WO 90/03536 | 4/1990 |
| WO | WO 98/19724 | 5/1998 |
| WO | WO 99/27886 | 6/1999 |
| WO | WO 99/62578 | 12/1999 |
| WO | WO 00/05292 | 2/2000 |
| WO | WO 00/35517 | 6/2000 |
| WO | WO 01/80928 | 11/2001 |
| WO | WO 02/02048 | 1/2002 |
| WO | WO 02/11794 | 2/2002 |
| WO | WO 02/064077 | 8/2002 |
| WO | WO 02/076540 | 10/2002 |
| WO | WO 2006/082350 | 8/2006 |
| WO | WO 2006/083333 | 8/2006 |
| WO | WO 2008/115102 | 9/2008 |

OTHER PUBLICATIONS

Macmillan dictionary entry for "integrated." http://www.macmillandictionary.com/dictionary/american/integrated. Accessed Apr. 24, 2013.*

Taiwan Search Report for Taiwan Patent Application 092106323 dated Mar. 21, 2003 (4 pages).

Japan Application No. 2003-583539, Official Action dated May 1, 2009 (3 pages).

Japan Application No. 2003-577789, Official Action dated Feb. 24, 2009 (4 pages).

International Search Report, PCT/EP2008/067535 dated Oct. 13, 2009 (3 pages).

International Search Report, PCT/EP2008/067522 dated Aug. 12, 2009. (2 pages).

Sasaki, United States Patent Office, Final Office Action, U.S. Appl. No. 11/762,550, mailed Mar. 17, 2010 (11 pages).

Sasaki, United States Patent Office, Non-Final Office Action, U.S. Appl. No. 11/762,550, mailed Jun. 12, 2009 (11 pages).

* cited by examiner

DEVICE FOR PROVIDING FLUID TO A RECEPTACLE

TECHNICAL FIELD

The invention relates to a device for providing cleaned fluid i.e. gas and/or liquid to a receptacle.

The invention can be implemented in aseptic preparation of drugs, for example for providing sterilized/cleaned air to a medical receptacle, such as a bottle or vial, with the purpose of drawing a solution or another liquid used in medicine applications out from the medical receptacle.

BACKGROUND OF THE INVENTION

In the field of drug preparation for injection or infusion generally two basic problems have to be considered. Firstly, certain demands are made on aseptic conditions so as to avoid contamination of the drug, and, secondly, the drug has to be handled in such a way that drug leakage to the environment is prevented or minimized. By a sterile or aseptic handling of the drug, the risk for transferring bacteria or any other undesired substance to the patient is reduced. By preventing drug leakage to the environment, the exposure of medical and pharmacological staff to hazardous drugs is decreased.

In order to achieve aseptic conditions special safety boxes, cabinets or isolators are being used where the air is filtered through HEPA filters to prevent contamination during preparation of drugs. Ventilated cabinets are also used to reduce uncontrolled leakage to the environment and prevent occupational exposure to possibly hazardous drugs. Such facilities, however, require a lot of space and are associated with relatively high costs. Furthermore, the offered protection can be insufficient and working environment problems due to accidental exposure to drugs, for example cytotoxins, have been reported.

Another solution of the problems mentioned above is to create a so called “closed” or “non-vented” system for handling the drugs during preparation. Such systems exist and enable the preparation to be accomplished without the use of special safety boxes, cabinets or isolators. In such a closed system the drugs are handled isolated from the environment during every single step so as to avoid contamination of the drug and undesired drug leakage to the environment.

A known problem associated with the preparation of drug solutions is the fact that medical bottles or vials normally are made of a non-compressible material, such as glass or plastic. To enable the vial to be drained off, air has to flow into the vial so as to avoid negative pressure in the vial which negative pressure would otherwise counteract or prevent further transportation of liquid from the vial to another receptacle such as syringe.

A system for providing sterilized gas is disclosed in WO 00/35517. A flexible bag containing sterilised gas is provided. The bag has an opening covered by a gas and liquid-impervious membrane which can be punctured by a needle in order to draw the sterilised gas out from the bag for further transportation of the gas to a bottle. A bottle connector is arranged on the current bottle and the bottle connector has a pressure compensation means for receiving gas. By use of a syringe and an injector device provided with a needle the sterilised gas is transferred from the flexible bag to the bottle and to the pressure compensation means arranged on the bottle connector. Thereafter the substance in the bottle can be drawn out from the bottle by means of the injector device while the sterilised gas flows from the pressure compensation means into the bottle.

However, the prior art system described in WO 00/35517 has drawbacks. The system comprises several components to be handled and further the sterilised gas has to be drawn from the flexible bag by means of an injector device provided with a needle, and subsequently transferred to the bottle and the pressure compensation means. Consequently, several manipulations have to be accomplished before the medical substance can be drawn from the bottle.

In WO 02/11794 a system for providing cleaned gas is described. This system works with an injection syringe and an air filter to be attached to a connection nozzle of the syringe. The container of the syringe is charged with air which has been forced through the filter so as to clean the air. Thereafter the air filter is removed and the syringe is connected to a coupling means (injector device) which in turn is connected to a capping means (bottle connector) arranged on a bottle. The capping means has a pressure-equalisation chamber whose volume can vary. The cleaned gas in the syringe is transferred from the syringe to the bottle and to the pressure-equalisation chamber arranged on the capping means. Thereafter the substance in the bottle can be drawn out from the bottle by means of the syringe and the coupling means, while the cleaned gas flows from the pressure-equalisation chamber into the bottle.

Also the prior art system described in WO 02/11794 has drawbacks. The system requires an adapter provided with an air filter being connected to and removed from a syringe in order to fill the pressure-equalisation chamber before the medical substance can be drawn from the bottle. In an alternative embodiment the air filter is fixedly attached to a syringe. However, in such a case a conventional syringe can not be used. In both cases, the cleaned gas has to be drawn from the environment and subsequently transferred to the bottle and the pressure-equalisation chamber before the medical substance can be drawn from the bottle.

SUMMARY OF THE INVENTION

An object of the invention is to provide a device for providing cleaned and/or sterilized fluid of the kind referred to in the introduction where at least one problem of such prior art devices discussed above is reduced to a substantial extent. In particular, the invention aims to indicate how to provide sterilized/cleaned fluid in a rational and safe way during preparation of drugs.

The invention is based on the insight that sterilized/cleaned air is advantageously provided by a connector system itself, rather than utilising additional equipments to fill an expansion container comprised in a connector system during drug preparation. However, a container has to be filled with the fluid either during manufacturing of the device or by the user, and these two options result in two aspects of the invention.

According to a first aspect of the invention the object is achieved by a device according to claim 1.

By the provision of a connector and a container which form an integrated unit, wherein the connector is provided with a first means for connection to a receptacle, and the container is pre-filled or adapted to be pre-filled with a sterilized or cleaned fluid to be transferred from the container to a receptacle interconnected with the connector during conveyance of a substance out of the receptacle, no additional flexible bag filled with sterilized/cleaned fluid is needed. The handling is simplified since no syringe provided with a needle is to be used for transferring sterilized/cleaned fluid into for example a vial before conveyance of a substance out of the vial. The pre-filled container replaces both the additional flexible bag and the pressure compensation means needed in the prior art devices. Conveyance of a substance out from the receptacle can be accomplished as soon as the connector is arranged on the receptacle.

According to a second aspect of the invention the object is achieved by a device according to claim 10.

By the provision of a connector and a container which form an integrated unit, wherein the connector is provided with a first means for connection to a receptacle, and the integrated unit is provided with a filter for cleaning fluid passing the filter during filling the container with fluid, for example before connection of the connector to a receptacle, no syringe provided with an air filter adapter or an air filter fixedly attached to the syringe is needed for transferring cleaned fluid into for example a vial before conveyance of a substance out of the vial. Instead a conventional syringe can be used for conveyance of a substance out from the receptacle as soon as the connector is arranged on the receptacle.

On comparison the two aspects of the invention it can be established that the device according to the first aspect does not exhibit any filter which saves costs as to the production of the device. Furthermore, the degree of purity which can be obtained during manufacturing of the device, for example by sterilization, is very high and in most cases very important. On the other hand the device according to the second aspect can have a decreased volume which could result in smaller package and save shipment costs. In many applications a cleaned fluid suitable for aseptic preparation of drugs can be achieved by filtering the fluid.

BRIEF DESCRIPTION OF THE DRAWINGS

With reference to the appended drawings, below follows a more detailed description of embodiments of the invention cited as examples.

In the drawings.

DETAILED DESCRIPTION OF PREFERRED EMBODIMENTS OF THE INVENTION

Figure 1:
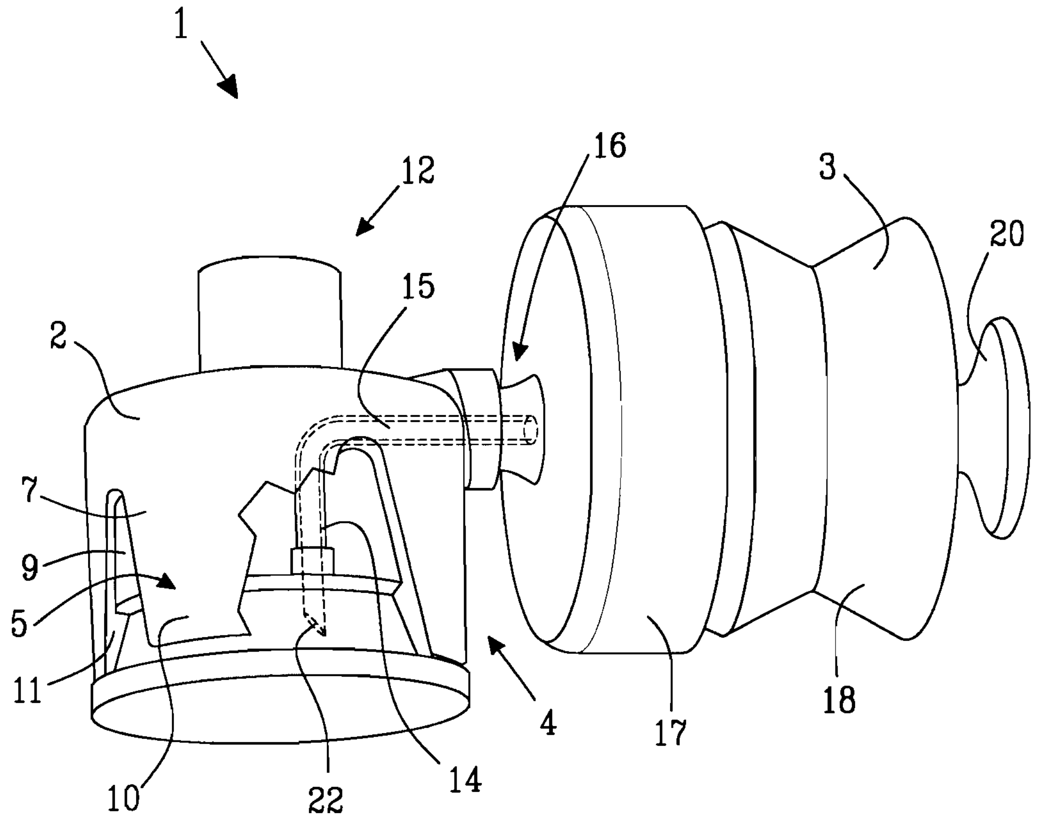
FIG. 1 is a perspective view of a device according to a first aspect of the invention.
Figure 2:
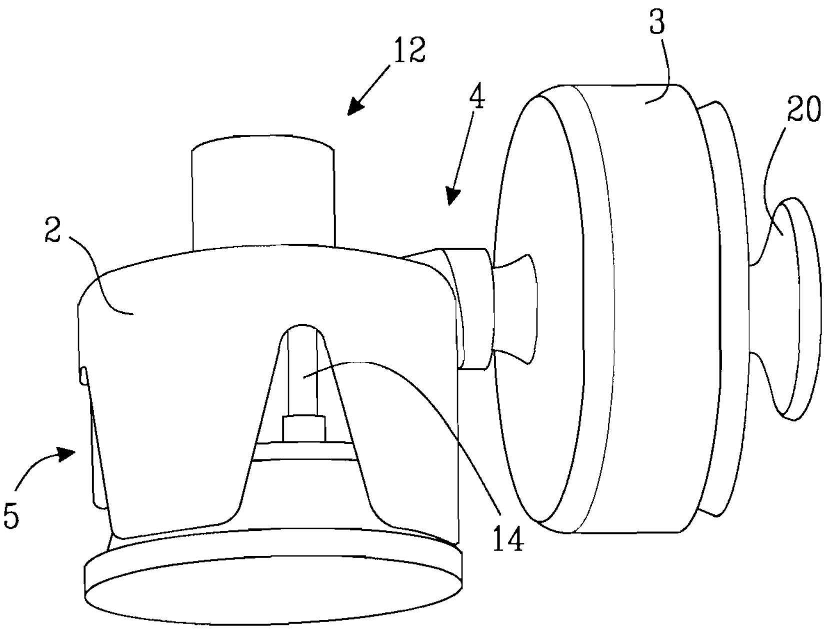
FIG. 2 is a view corresponding to FIG. 1 illustrating the device in another condition.
Figure 3:
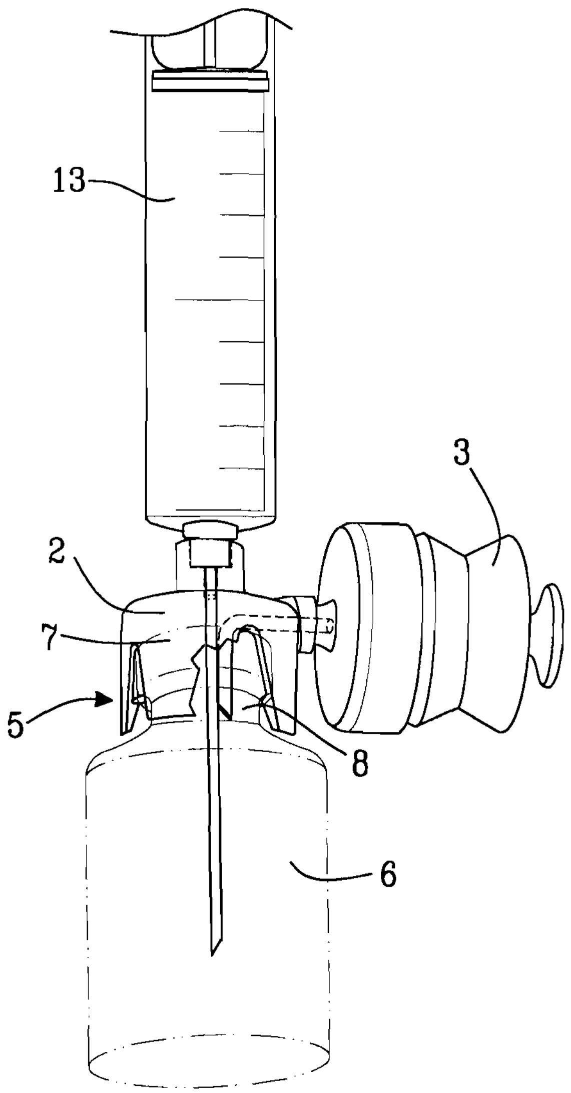
FIG. 3 is a perspective view of the device according to FIG. 1 connected to a vial.
Figure 4:
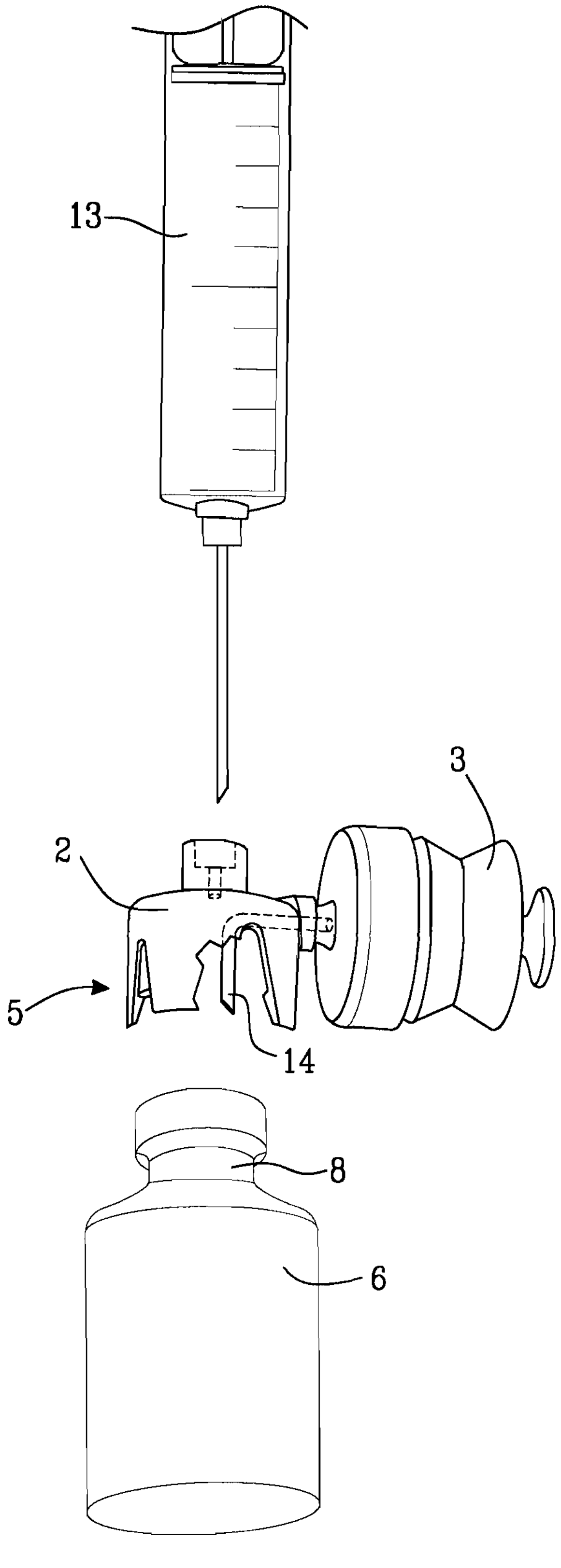
FIG. 4 is an exploded view corresponding to FIG. 3.

In FIGS. 1 and 2 a device 1 according to the first aspect of the invention is illustrated. The device 1 can be used for providing cleaned and/or sterilized gas, for example air, to a receptacle and thereby facilitate conveyance of a substance out of the receptacle. Such a substance can be various solutions and liquids constituting drugs, for example cytotoxic drugs and antibiotics, for use in the field of medicine. The device comprises a connector 2 and a container 3 which form an integrated unit 4. The connector 2 is provided with a first means 5 for connection to a receptacle or in other words a first connector portion 5 for connection to a receptacle. The container 3 is pre-filled or adapted to be pre-filled with a cleaned and/or sterilized gas to be transferred from the container 3 to a receptacle, which is connectable with the connector 2, during conveyance of a substance out of the receptacle. Se also FIG. 3 illustrating the device 1 connected to a medicine receptacle such as a bottle or vial 6, and the exploded view in FIG. 4. By the expression "pre-filled" is meant the container being already filled with gas before it is used for providing gas to a receptacle. The device is suitably already filled when delivered to the user, and preferably the container is filled during or after manufacture of the device for example just before or at the moment when the device is enclosed by a package or packing.

By the expression "cleaned" gas is meant that the gas has been filtered by a filter to remove particles and/or viable micro-organisms to such an extent that the gas is classified to be aseptic and accepted by the relevant authority and/or any standards. The degree of purity can be expressed in the largest particles allowed to pass the filter for a given flow rate of gas. In some cases no or very few particles having a size exceeding 5 μm are allowed to be present in the cleaned gas. However, the allowed particle size is determined by the requirements in the current application. Some drug treatments require that substantially all particles having a size exceeding 0.15 μm are removed from the gas by the particulate air filter. As an example, a filter with the mesh size 0.2 μm can be used to remove substantially all particles and micro organisms of that size or larger.

By the expression "sterilized" gas is meant that the gas has been subjected to a sterilization method to remove viable micro-organisms, which method is accepted for the current product by the relevant authority. Current regulations in Europe for medical devices to be designated "STERILE" may be found in the European standard EN 556-1. Other regulations may exist in other countries. The sterilization can be ethylene oxide sterilization, sterilisation by irradiation, or (moist) heat sterilization or any other accepted method. The European standard requirements imply that the theoretical probability of there being a viable micro-organism present on/in the sterilized device shall be equal to or less than $1\times10^{-6}$.

In the case the gas is sterilized, it is not always necessary to clean the gas according to the cleaning process as described above, although such cleaning and the sterilization can be combined. However, other methods can be used to remove particles etc. from the gas if required or the sterilization process itself may be sufficient to bring the gas into a state where the gas is to be considered as both cleaned and sterilized.

The first connection means 5 can be designed for connection to a receptacle, such as the neck of a vial. In the embodiment illustrated in FIGS. 1-4, the first connection means 5 is constituted by a ring-shaped portion 7 for enclosing the neck 8 of the vial 6. The ring-shaped portion 7 has slits 9 so as to form flanges 10 which protrude downwardly. The flanges 10 can be provided with hooks 11 or barbs for gripping around the neck 8 of the vial 6. The connector 2 is suitably provided with a second means 12 for connection to a transfer member 13 (see FIGS. 3 and 4), such as an injector device to be interconnected with the connector, for conveyance of a substance out of the receptacle 6. In other words; the connector 2 is suitably provided with a second connector portion 12.

In another embodiment (not shown) of the invention the second connection means 12 can comprise a luer lock coupling or bayonet coupling to enable an injector device to be connected to the connector. Suitably, both the injector device and the connector are provided with a membrane so as to create a double membrane coupling between the injector and the current device.

The amount of gas, preferably air, provided by the pre-filled container, should be adapted to the volume of the receptacle which is to be drained off. The volume of the gas when being in the receptacle should preferably correspond to the volume of the receptacle so as to enable the receptacle to be completely drained off. This implies that the volume of the cleaned or sterilized gas in the pre-filled container is preferably approximately equal to or larger than the volume of the receptacle provided that the pressure of the gas is substantially the same in the receptacle as in the container. For most medicine receptacles the volume of the gas should be in the interval 1-100 $cm^3$ at atmospheric pressure.

The connector 2 is preferably provided with a piercing member, such as a hollow needle 14 (as illustrated) for penetration of a closing (not illustrated) made of rubber for instance, which closing covers the opening of a receptacle 6, such as a vial. In addition to injection needles or cannulae, the expression "needle" is meant to comprise spikes and similar components for penetration of such a closing in order to create a channel between the container 3 and the receptacle 6 to which the connector 2 is connected. By a channel or passage 15 inside the needle 14, gas contained in the container 3 can be transferred from the container to the receptacle 6, i.e. gas can flow from the container 3 to the receptacle 6.

The connector 2 and the container 3 form an integrated unit 4. This implies that the connector and the container are made in one piece or the connector 2 and the container 3 can be coupled to each other so as to form an integral unit 4. Different types of coupling means known from prior art can be used as long as an airtight, or at least a substantially airtight connection can be obtained between the current components 2, 3.

The volume of the container 3 can be variable so as to allow the gas to flow from the container 3 to a receptacle 6. The container 3 is suitably made of a compressible material to make the volume of the container variable. To obtain a container 3 having a variable volume the container can comprise a first portion 17 made by a relatively rigid material which first portion 17 is coupled to the connector 2, and a second portion 18 made by a relatively flexible material attached to the first portion 17. For example, the container 3 can be designed to have a flexible portion, such as a bellow which is compressible and extendable. According to an embodiment of the invention, the container, or the flexible portion of the container, comprises a displaceable spring-loaded element, such as an axial spring-loaded element, that is arranged to allow fluid to flow into the container/flexible portion of the container. The displaceable spring-loaded element is for example constrained between two flanged ends of the flexible portion. When the flexible portion is empty the spring(s) of the spring-loaded element is/are highly compressed. As the flexible portion is filled with fluid the spring(s) of the spring-loaded element become(s) less compressed. The spring(s) may be arranged on the inside or outside of the flexible portion or they may be integrally formed with the flexible portion. The displaceable spring-loaded element may be arranged to be disconnected from the container/flexible portion of the container once the container/flexible portion of the container has been filled to the desired amount.

According to an embodiment the flexible portion of the container may be arranged to be detachable from the remaining part of the container, whereby the flexible portion may be filled with fluid before and/or after it has been attached to the remaining part of the container. Hereby the volume of the container 3 can be increased and decreased, respectively. Although the device illustrated in FIG. 1 comprises a compressible container, in another embodiment the container can have a cylinder and a piston arranged therein so as to enable the volume of the container to be changed.

According to an embodiment of the invention the container comprises locking means to prevent fluid from flowing into the container, during the transportation of the device, for example, or at any other time when the device is not in use.

Alternatively to a collapsible container, or in combination with a collapsible container, the container 3 can be pressurized by cleaned or sterilized gas to cause an overpressure in the container. An overpressure allows gas to flow from the container 3 to a receptacle 6 connected to the connector and the container. In such a case the container 3 does not necessarily need to be collapsible. The overpressure is suitably adapted to the size of the receptacle to which the connector is to be connected to ensure the receptacle can be completely drained off in a subsequent step. The pressure in the filled container can be for example in the interval from 1 atm to 2 atm. Preferably, the device comprises any means, such as a valve, for allowing the gas to flow from the container after the device has been connected to the receptacle and during conveyance of a substance out of the receptacle.

Figure 5:
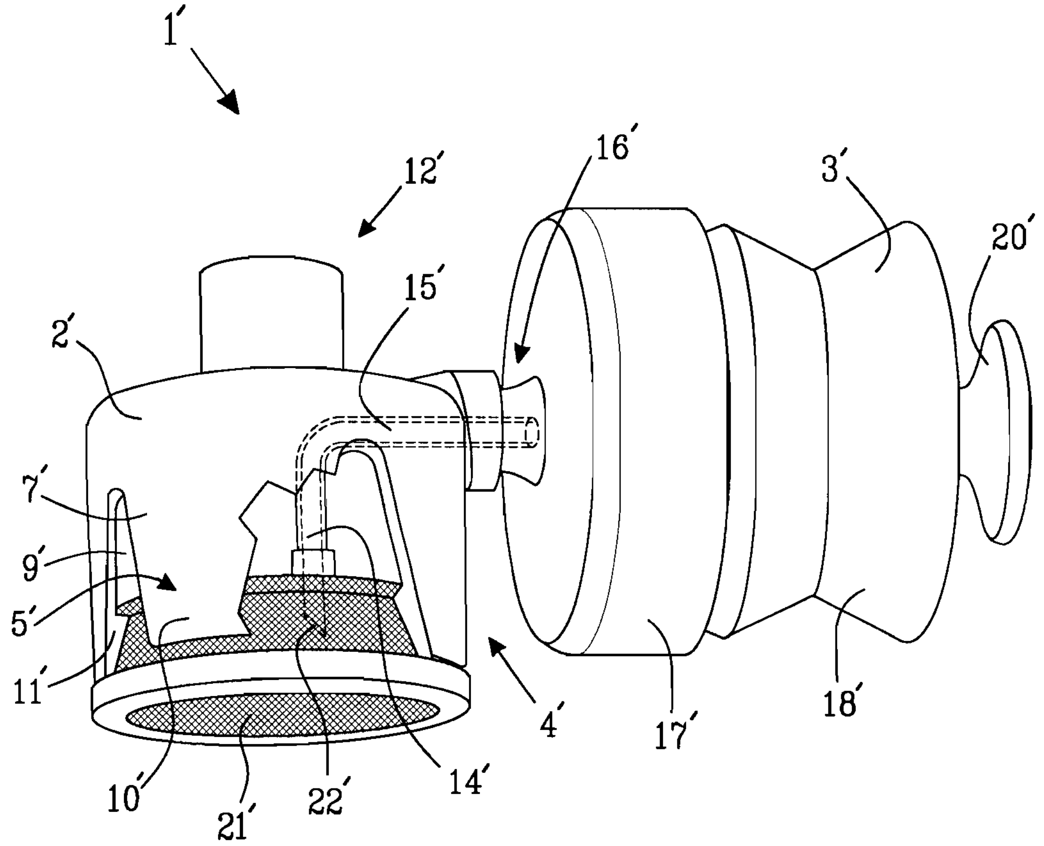
FIG. 5 is a perspective view of a device according to a second aspect of the invention.
Figure 5B:
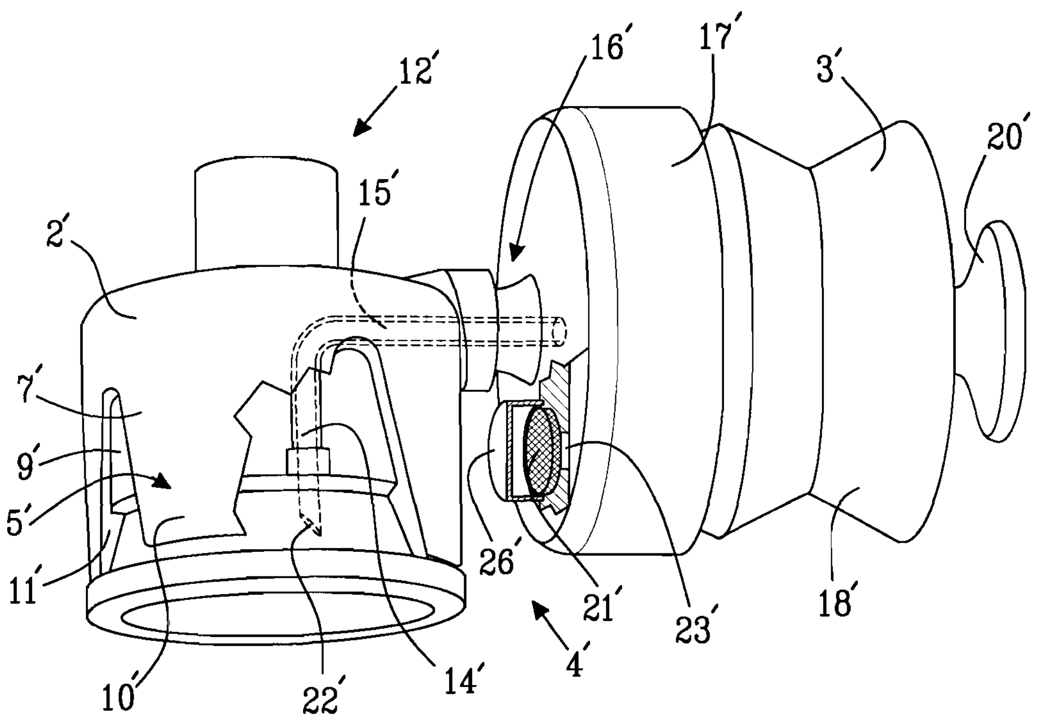
FIG. 5*b* is an alternative embodiment of the device illustrated in FIG. 5.
Figure 6:
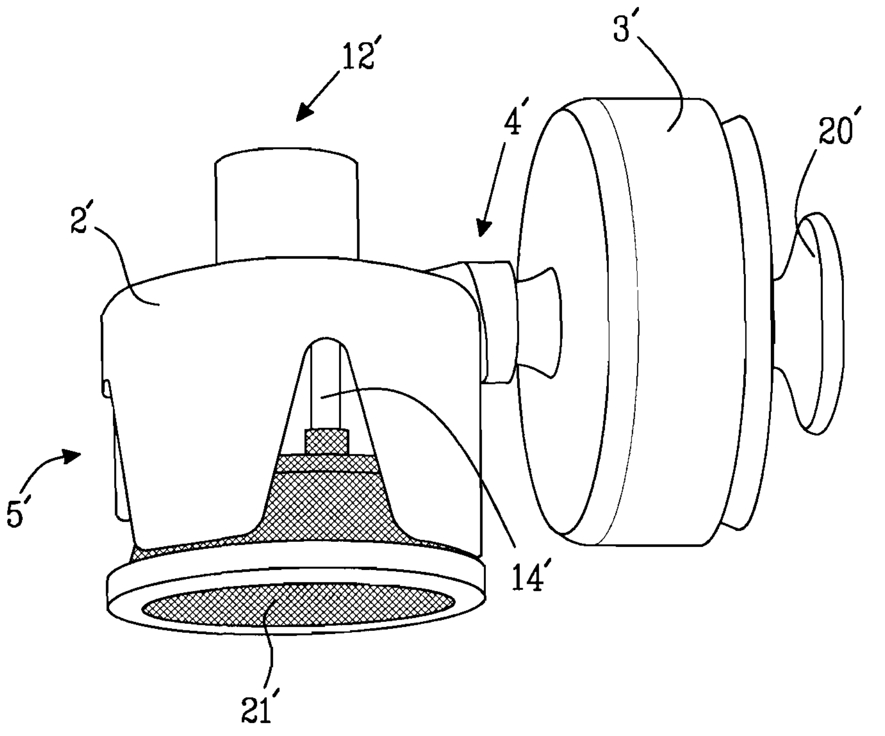
FIG. 6 is a view corresponding to FIG. 5 illustrating the device in another condition.
Figure 7:
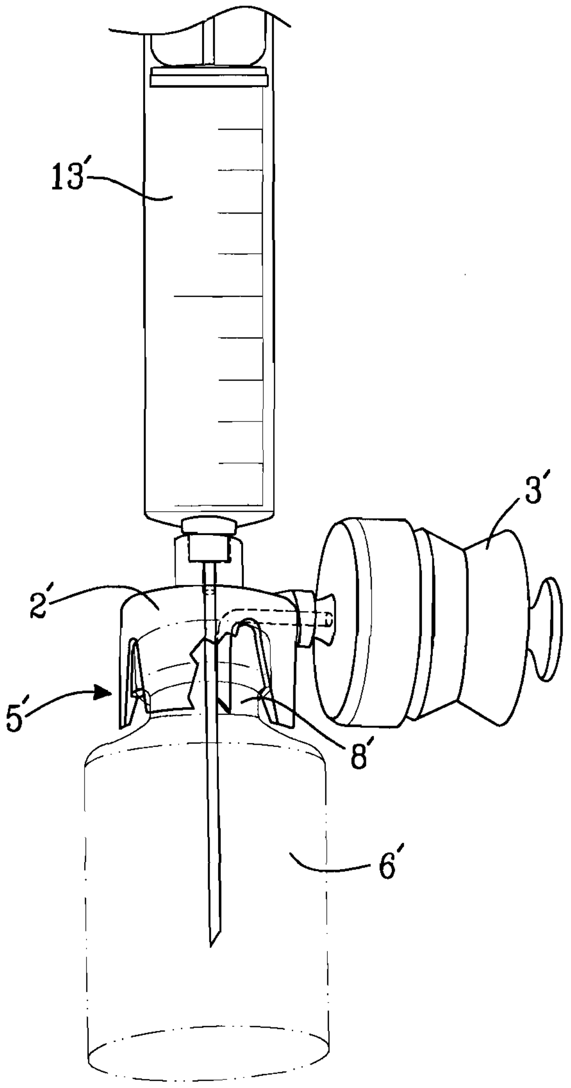
FIG. 7 is a perspective view of the device according to FIG. 5 connected to a vial.
Figure 8:
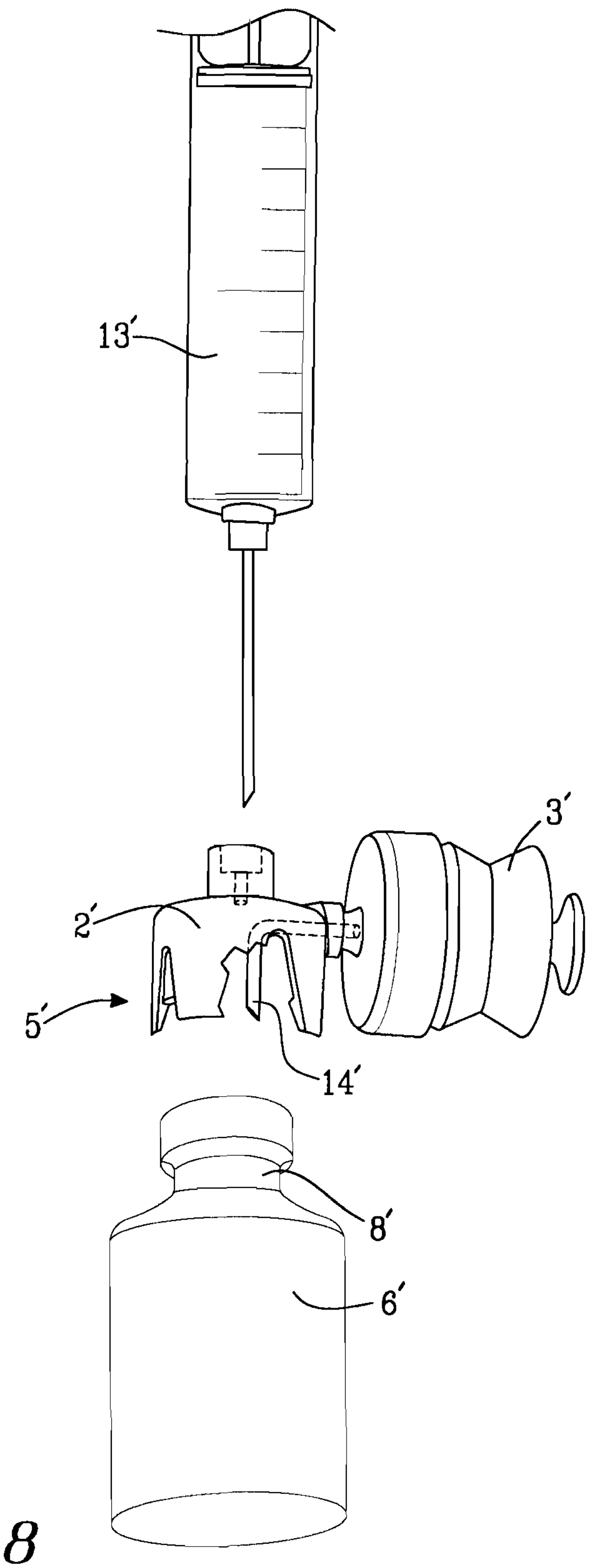
FIG. 8 is an exploded view corresponding to FIG. 7.

In FIGS. 5, 5*b* and 6 a device 1' according to the second aspect of the invention is illustrated. The device can be used for providing cleaned gas to a receptacle and thereby facilitate conveyance of a substance out of the receptacle. Such a substance can be various solutions and liquids constituting drugs, for example cytotoxic drugs or antibiotics, for use in the field of medicine. The device comprises a connector 2' and a container 3' which form an integrated unit 4'. The connector 2' is provided with a first means 5' for connection to a receptacle 6' or in other words a first connector portion 5'. See also FIG. 7 illustrating the device connected to a medicine bottle or vial 6', and the exploded view in FIG. 8.

The first connection means 5' can be designed for connection to a bottle, such as the neck of a vial. In the embodiment illustrated in FIGS. 5-8, the first connection means 5' is constituted by a ring-shaped portion 7' for enclosing the neck 8' of the vial 6'. The ring-shaped portion 7' has slits 9' so as to form flanges 10' which protrude downwardly. The flanges 10' can be provided with hooks 11' or barbs for gripping around the neck 8' of the vial 6'. The connector 2' is suitably provided with a second means 12' for connection to a transfer member 13', such as an injector device to be interconnected with the connector, for conveyance of a substance out of the receptacle 6'. In other words; the connector 2' is suitably provided with a second connector portion 12'.

In another embodiment (not shown) of the invention the second connection means 12' can comprise a luer lock coupling or bayonet coupling to enable an injection device to be connected. As already described for the device according to the first aspect of the invention, both the injector device and the connector are suitably provided with a membrane so as to create a double membrane coupling between the injector and the current device.

The connector 2' is preferably provided with a piercing member, such as a hollow needle 14' (as illustrated) for penetration of a closing (not illustrated) made of rubber for instance, which closing covers the opening of a receptacle 6, such as a vial. In addition to injection needles or cannulae, the expression "needle" is meant to comprise spikes and similar components for penetration of such a closing in order to create a channel between the container 3' and the receptacle 6' to which the connector 2' is connected. By a channel or passage 15' in the needle 14', gas contained in the container 3' can be transferred from the container to the receptacle 6', i.e. gas can flow from the container 3' to the receptacle 6'.

The connector 2' and the container 3' form an integrated unit 4'. This implies that the connector and the container are made in one piece or the connector 2' and the container 3' can be coupled to each other so as to form an integral unit. Different types of coupling means 16' known from prior art can be used as long as an airtight or at least a substantially airtight connection can be obtained between the current components 2', 3'.

The container 3' has to be filled with gas before connection of the connector 2' to a receptacle 6'. The volume of the container 3' is preferably variable. To obtain a container 3' having a variable volume the container can comprise a first portion 17' made by a relatively rigid material which first portion is coupled to the connector 2', and a second portion 18' made by a relatively flexible material attached to the first portion 17'. The second portion 18' can be extensible by manipulation of for example a handle 20' arranged at the end of the container 3'. Hereby the volume of the container 3' can be increased and decreased, respectively. For example, the container 3' can be designed to have a flexible portion, such as a bellow which is compressible and extendable by affecting the container manually. The container 3' is preferably provided with said handle 20' for regulating the volume of the container 3'. Although the volume of the container is preferably variable as illustrated, there may be other ways to fill the container while at the same time ensuring the gas passes a filter 21'. For example, the gas container could be constituted by a sealed vacuum-packed flexible bag whose seal can be broken to allow gas to flow into the bag. Alternatively, the gas container is rigid or semi-rigid and pressurized gas is used to fill the container.

The amount of gas, preferably air, provided by the pre-filled container, should be adapted to the volume of the receptacle which is to be drained off. The volume of the gas when being in the receptacle should preferably correspond to the volume of the receptacle so as to enable the receptacle to be completely drained off. This implies that the volume of the cleaned or sterilized gas in the pre-filled container is preferably approximately equal to or larger than the volume of the receptacle provided that the pressure of the gas is substantially the same in the receptacle as in the container. For most medicine bottles or vials, the volume of the gas should be in the interval 1-100 $cm^3$ at atmospheric pressure.

Thus, the integrated unit 4' is provided with the filter 21', such as a particulate air filter for cleaning gas passing the filter 21' during filling the container 3' with gas, preferably by increasing the volume of the container 3', before connection of the connector 2' to a receptacle 6'. Although the filter, hereinafter called particulate air filter 21' can be arranged in different ways, according to the embodiment illustrated in FIGS. 5 and 6 the particulate air filter 21' is arranged on the connector 2'. By covering the opening of the needle 14' by means of the particulate air filter 21', it is ensured that the gas which is brought into the container 3' has to pass the particulate air filter 21'. The particulate air filter 21' is arranged to be removed from the integrated unit 4' after the container 3' has been filled with cleaned gas. Subsequently to filling the container 3' the particulate air filter 21' is removed and the connector 2' is to be connected to the receptacle 6'.

By the expression "cleaned" gas is meant that the gas has been filtered by a filter to remove particles and/or viable micro-organisms to such an extent that the gas is classified to be aseptic and accepted by the relevant authority and/or any standards. The degree of purity can be expressed in the largest particles allowed to pass the filter for a given flow rate. In some cases no or very few particles having a size exceeding 5 μm are allowed to be present in the cleaned gas. However, the allowed particle size is determined by the requirements in the current application. Some drug treatments require that substantially all particles having a size exceeding 0.15 μm are removed from the gas by the particulate air filter. As an example, a filter with the mesh size 0.2 μm can be used to remove substantially all particles and micro organisms of that size or larger.

The particulate air filter 21' is preferably designed as a needle shield 22' for the tip of needle 14'. The filter can be arranged to at least partially cover or surround the tip of the needle 14'. This implies that the particulate air filter 21' cleans the gas and at the same time the particulate air filter 21' functions as a protection during handling of the device 1'. Furthermore, such a needle tip shield 22' protects the sterile package enclosing the device during transport and storage of the device.

By removing the particulate air filter 21', after the container 3' has been filled with the gas and prior to interconnection of the connector 2' and the receptacle 6' to each other, any contamination particles removed from the gas and collected in the particulate air filter 21' are removed from the integrated unit 4'. Thus, one and the same channel can be used for both filling the container 3' with cleaned gas and transferring the cleaned gas from the container 3' to a receptacle 6'.

In the embodiment illustrated in FIG. 5*b* where the particulate air filter 21' is not to be removed before interconnection of the connector 2' and the receptacle 6' to each other, the particulate air filter 21' has to be arranged so as to avoid contamination during transportation of the gas from the container 3' to the receptacle 6'. The integrated unit 4' can be provided with a first channel 23' for filling the container 3' with cleaned gas and a second channel 15' for transferring the cleaned gas to a receptacle. Otherwise, i.e. if the particulate air filter is to be left, and one and the same channel is used for transportation of gas in both directions; the particles collected in the particulate air filter could possibly release from the particulate air filter and be unintentionally brought into the receptacle 6' by the gas flow. Such a contamination can be prevented by providing a removable air filter or by providing different openings/channels for transportation of gas into and out of the container 3', respectively.

A lid 26' can be arranged on the integrated unit 4' for covering the particulate air filter 21' so as to prevent further communication between the interior of the integrated unit 4' and the environment via the particulate air filter 21' after filling the container 3'. Firstly, the container 3' is filled with the cleaned gas and thereafter the lid 26' is mounted on the integrated unit 4' to cover the particulate air filter 21' and prevent further gas transportation through the air particle filter 21'. Thereafter, the integrated unit 4' and the receptacle 6' are to be interconnected and the subsequent manipulations can be safely executed.

The lid 26' has the function of preventing transportation of liquid, gas or any vapour in the direction from the integrated unit 4' to the environment so as to counteract that any undesired substance in the receptacle 6' escapes to the environment.

It is to be understood that the present invention is not limited to the embodiments described above and illustrated in the drawings; rather, the skilled person will recognize that many changes and modifications may be made within the scope of the appended claims. For example, the invention can be applied to other medical applications and there may be additional purposes for providing cleaned or sterilized gas to a receptacle.

The invention claimed is:

1. A device for facilitating conveyance of a substance out of a receptacle, comprising a connector and a container which form an integrated unit, wherein said connector comprises a first connector element for connection to said receptacle, said container is designed to have a flexible portion, said container or said flexible portion comprises a displaceable spring-loaded element that is arranged to allow fluid to flow into said container or said flexible portion wherein said container is pre-filled with a cleaned fluid to be transferred from said container to said receptacle, wherein said receptacle is connectable to said connector element of said connector, during conveyance of a substance out of said receptacle, wherein said cleaned fluid is gas, liquid, or a combination of gas and liquid, and wherein conveyance of said substance out of said receptacle is capable of occurring as soon as said connector element is arranged on said receptacle since cleaned fluid will be transferred from said container to said receptacle as said substance is conveyed out of said receptacle, wherein said container and receptacle are positioned orthogonal to each other.

2. A device according to claim 1, wherein said fluid is sterilized.

3. A device according to claim 1 or 2, wherein the volume of the container is variable.

4. A device according to claim 3, wherein said container is made of a compressible material to make the volume of the container variable.

5. A device according to claim 3, wherein the container comprises a locking element configured to prevent fluid from flowing into the container.

6. A device according to claim 3, wherein said connector comprises a second connector element for connection to a transfer member for conveyance of a substance out of a receptacle.

7. A device according to claim 1, wherein said container is pressurized by cleaned or sterilized fluid to cause an overpressure in the container which overpressure is adapted to the size of the receptacle to which the connector is to be connected.

8. A device for facilitating conveyance of a substance out of a receptacle, comprising a connector and a container which form an integrated unit, wherein said connector comprises a first connector element for connection to said receptacle, said container comprises a bellow that is collapsible and extendable by affecting the container manually by a user wherein said container is pre-filled with a cleaned fluid to be transferred from said container to said receptacle, wherein said receptacle is connectable to said connector element of said connector, during conveyance of a substance out of said receptacle, wherein said cleaned fluid is gas, liquid, or a combination of gas and liquid, and wherein conveyance of said substance out of said receptacle is capable of occurring as soon as said connector element is arranged on said receptacle since cleaned fluid will be transferred from said container to said receptacle as said substance is conveyed out of said receptacle, wherein said container and receptacle are positioned orthogonal to each other.

9. A device according to claim 8, wherein said fluid is sterilized.

10. A device according to claim 8, wherein the volume of the container is variable.

11. A device according to claim 10, wherein said container is made of a compressible material to make the volume of the container variable.

12. A device according to claim 10, wherein the container comprises a locking element configured to prevent fluid from flowing into the container.

13. A device according to claim 10, wherein said connector comprises a second connector element for connection to a transfer member for conveyance of a substance out of a receptacle.

14. A device according to claim 8, wherein said container is pressurized by cleaned or sterilized fluid to cause an overpressure in the container which overpressure is adapted to the size of the receptacle to which the connector is to be connected.

* * * * *